United States Patent [19]
Breitenfelder et al.

[11] Patent Number: 4,928,684
[45] Date of Patent: May 29, 1990

[54] APPARATUS FOR ASSISTING THE SPONTANEOUS RESPIRATION OF A PATIENT

[75] Inventors: Wilheim Breitenfelder, Friedberg; Fritz Trenkner, Taunus, both of Fed. Rep. of Germany

[73] Assignee: Salvia-Werk Gesellschaft zur Herstellung chemischer and pharmazeutischer Erzeuginisse mbH, Saar, Fed. Rep. of Germany

[21] Appl. No.: 354,610

[22] Filed: May 22, 1989

[30] Foreign Application Priority Data

May 27, 1988 [DE] Fed. Rep. of Germany ....... 3817985

[51] Int. Cl.$^5$ ............................................ A61M 16/00
[52] U.S. Cl. .......................... 128/204.21; 128/204.23
[58] Field of Search ...................... 128/204.18, 204.21, 128/204.22, 204.23, 204.24, 204.25, 204.26, 205.11, 205.24, 671, 685, 716, 719, 720, 725

[56] References Cited

U.S. PATENT DOCUMENTS

| 3,946,729 | 3/1976 | Hanna | 128/204.23 |
|---|---|---|---|
| 3,961,627 | 6/1976 | Ernst et al. | 128/204.21 |
| 3,974,828 | 8/1976 | Bird | 128/204.25 |
| 4,206,754 | 6/1980 | Cox et al. | 128/204.21 |
| 4,345,612 | 8/1982 | Koni et al. | 128/204.21 |
| 4,380,233 | 4/1983 | Caillot | 128/204.21 |
| 4,393,869 | 7/1983 | Boyarsky et al. | 128/204.18 |
| 4,635,631 | 1/1987 | Izumi | 128/204.23 |
| 4,648,395 | 3/1987 | Sato et al. | 128/204.23 |
| 4,677,975 | 7/1987 | Edgar et al. | 128/204.23 |
| 4,681,099 | 9/1987 | Sato et al. | 128/204.23 |

Primary Examiner—Eugene H. Eickholt
Attorney, Agent, or Firm—Armstrong, Nikaido, Marmelstein, Kubovcik & Murray

[57] ABSTRACT

An apparatus for assisting the spontaneous breathing of a patient includes mixing unit (1) for mixing air and oxygen has an air-flow sensor (8), an electrically controlled air valve (7), an oxygen-flow sensor (9), and an electrically controlled oxygen valve (7). A respiratory-gas pressure sensor (20) is disposed on a gas duct (15) which connects the respiratory-gas unit (1) to an outlet (16). An electrically controlled outlet valve (17) is placed on the outlet (16). The air-flow sensor (8), the oxygen-flow sensor (9), the respiratory-gas pressure sensor (20), the air valve (6), the oxygen valve (7) and the outlet valve (16) are connected to an electronic control unit (40). The sensor signals produce input variables for the control unit. The control unit delivers control signals for the valves.

10 Claims, 1 Drawing Sheet

APPARATUS FOR ASSISTING THE SPONTANEOUS RESPIRATION OF A PATIENT

BACKGROUND OF THE INVENTION

The invention relates to a machine for assisting the spontaneous respiration of a patient, having a respiratory-gas mixing unit for mixing air and oxygen in a desired ratio in order to supply the patient with respiratory gas of an adjustable oxygen concentration, an outlet on which are disposed a pressure regulator, a gas duct connecting the respiratory-gas mixing unit to the outlet, and a patient line which branches off from the gas duct on a junction arranged between the respiratory-gas mixing unit and the outlet.

Patients who breathe spontaneously usually need no mechanical respiration. Nevertheless, it is frequently necessary, particularly within the purview of intensive care, to assist their respiration. This is done, for example, by raising the oxygen concentration relative to the normal oxygen content of the air and by a slight elevation of the pressure (by 3 to 15 mbar) in comparison with the normal air pressure.

To help the patient to get used to normal respiration, it is advisable to provide him continuously with respiratory gas having a largely constant pressure. Machines that assist the respiration of spontaneously breathing patients in this way are called "CPAP" (continuous positive airway pressure) machines.

Modern respirators frequently have the option of establishing a CPAP function. With these respirators, however, an adjustable trigger level must usually be exceeded to initiate the inspiration phase, and this can stress the patient. Moreover, respirators have a very complex technical design and are therefore expensive. Thus, their use for the CPAP function is uneconomical.

For these reasons, special machines of the type mentioned in the introduction have been developed. The respiratory gas is taken from the central air and oxygen supply systems normally present in the clinics and are mixed by means of mechanical respiratory-gas mixing units (so-called "oxyblenders"). A water lock is normally used as a pressure regulator at the outlet of the gas duct, whereby the immersion depth of the outflow orifice determines the level of the pressure. To damp the pressure fluctuations caused by the respiratory activity of the patient, large-volume, elastic accumulators are used.

In order to ensure the necessary constant respiratory-gas composition, a high degree of technical complexity must be designed into the machines of known construction. Nevertheless, uncertainties exist. Therefore, the machines must be monitored constantly by a qualified staff, or complex additional monitoring and alarm devices must be provided. Accordingly, the object of the invention is to provide a spontaneous-respiration-assisting machine which is improved in these respects and which can nevertheless be made inexpensively.

SUMMARY OF THE INVENTION

To achieve this object, it is suggested in a machine of the type defined in the introduction that the mixing unit include an air conduit and an oxygen conduit which are brought together in a mixing area, whereby there are installed on the air conduit an air-flow sensor for generating an electrical air-flow signal corresponding to the air flow and an electrically controlled air valve for adjusting the air flow, and there are placed on the oxygen conduit an oxygen-flow sensor for generating an electrical oxygen-flow signal corresponding to the oxygen flow, and an electrically controlled oxygen valve for adjusting the oxygen flow. Further, there is provided a respiratory-gas pressure sensor for generating an electrical signal corresponding to the respiratory-gas pressure of the machine. The pressure regulator disposed on the outlet is designed as an electrically controlled outlet valve, and the air-flow sensor, the oxygen-flow sensor, the respiratory-gas pressure sensor, the air valve, the oxygen valve and the outlet valve are connected to an electronic control unit. The sensor signals produce input variables for the control unit and the control unit delivers control signals as output variables for the valves.

The air line and the oxygen line of the mixing unit are connected to the corresponding central supply systems. The desired oxygen concentration and the desired respiratory pressure are ensured by several cooperating control loops.

A first control loop (respiratory-gas control) is used to ensure the desired constant respiratory pressure. Here, the respiratory-gas pressure sensor forms the primary actual-value sensor, whose actual signal is compared with the desired pressure. The pressure can now be controlled either through the total flow of the supplied fresh gas (oxygen and air) by means of the air valve and the oxygen valve, or the opening of the outlet valve can be properly controlled.

In a second and third control loop (air control loop and oxygen control loop), the air-flow sensor and the oxygen-flow sensor each form actual-value sensors for the corresponding flows, i.e., the quantity of gas flowing through the sensor per unit time. In the control unit, the ratio of the air-flow signal to the oxygen-flow signal is determined and compared with a set-point value that corresponds to the desired oxygen concentration. If the ratio of the flows differs from the desired set-point value, a corresponding correction is made by control signals that the control unit delivers to the air valve or to the oxygen valve. Thus, the second and third control loops form an oxygen-concentration control system.

The respiratory-gas pressure control system brings about a substantially synchronous opening and closing of the air valve and of the oxygen valve, whereby the oxygen-concentration control system controls the exact opening behavior and thus ensures the desired mixing ratio at all times.

In order that the patient be guaranteed a positive respiratory-gas pressure in every phase of the respiratory cycle, the total fresh-gas flow, also called "inlet flow", must always be greater than the maximum demand of the patient.

By means of the air valve and the oxygen valve in combination with the corresponding flow sensors, it is possible to adapt the inlet flow to the instantaneous needs of the patient at a given time. During the inspiration phase, the valves are opened and the pressure is controlled primarily by adapting the total fresh-gas flow to the patient's needs.

In the expiration phase, the air valve and the oxygen valve can to a large extent be closed, and the pressure is controlled by means of the outlet valve.

This rapid control, adapted to the instantaneous respiratory-gas needs of the patient at a given time (demand flow-principle), results in a particularly low gas consumption. Preferably the control is such, that the flow does not fall below a minimum fresh-gas flow (basic flow).

A surprising finding is that the solution to the problem according to the invention, seemingly complex at first glance, is on the whole attractive from an economical point of view. This is attributable, among other reasons, to the fact that it permits automatic monitoring of the machine functions and the patient's parameters.

For example, data can be stored in the control unit as to how the air flow must be changed as a function of the setting of the air valve and as to how the oxygen flow must be altered as a function of the setting of the oxygen valve, assuming normal operation and trouble-free gas supply. If the actual control behavior differs from these stored data by more than a specified tolerance margin, an alarm is triggered.

The total fresh-gas flow is an approximate measure of the respiratory needs of the patient. Great deviations can therefore be determined by means of the oxygen-flow signal and the air-flow signal. In this case as well, if a tolerance value relative to a set-point value stored in the control unit is exceeded, an alarm is triggered.

Considerably more accurate monitoring of the respiratory activity of the patient is possible in a preferred embodiment of the invention in which a flow sensor for producing an electrical outlet-flow signal corresponding to the gas flow on the outlet side is provided downstream from the branch pipe of the patient line and is connected to the control unit. Balancing is possible by comparing the outlet-flow signal with the sum of the air-flow signal and the oxygen-flow signal. The prevailing difference corresponds to the respiratory activity of the patient. Thus, a determination of the respiratory activity is possible with relatively little technical complexity without raising the respiratory resistance in the patient line and thus without stressing the patient.

Alternatively, however, it may also be advisable according to another modification of the invention, to provide a patient-flow sensor directly in the patient line, so that the patient-flow signal produced can be used for monitoring the respiratory activity.

According to a further embodiment of the invention, an additional total-fresh-gas-flow sensor for producing an electrical total-fresh-gas-flow signal corresponding to the total-fresh-gas flow is provided between the mixing area and the branch pipe of the patient line and is connected to the control unit as an additional input variable. The total-fresh-gas-flow signal must correspond to the sum of the air-flow-signal and the oxygen-flow signal provided the machine is operating correctly. In this way, monitoring of the oxygen concentration is possible without the need to place a special oxygen-measuring detector on the gas duct. As long as these flow signals coincide, it is ensured that the mixing ratio of air and oxygen—and thus the oxygen concentration—is also correct.

BRIEF DESCRIPTION OF THE DRAWING

The invention will now be explained in greater detail with reference to a specific embodiment shown schematically in the figure; in which.

DETAILED DESCRIPTION OF THE PREFERRED EMBODIMENT

Figure 1:
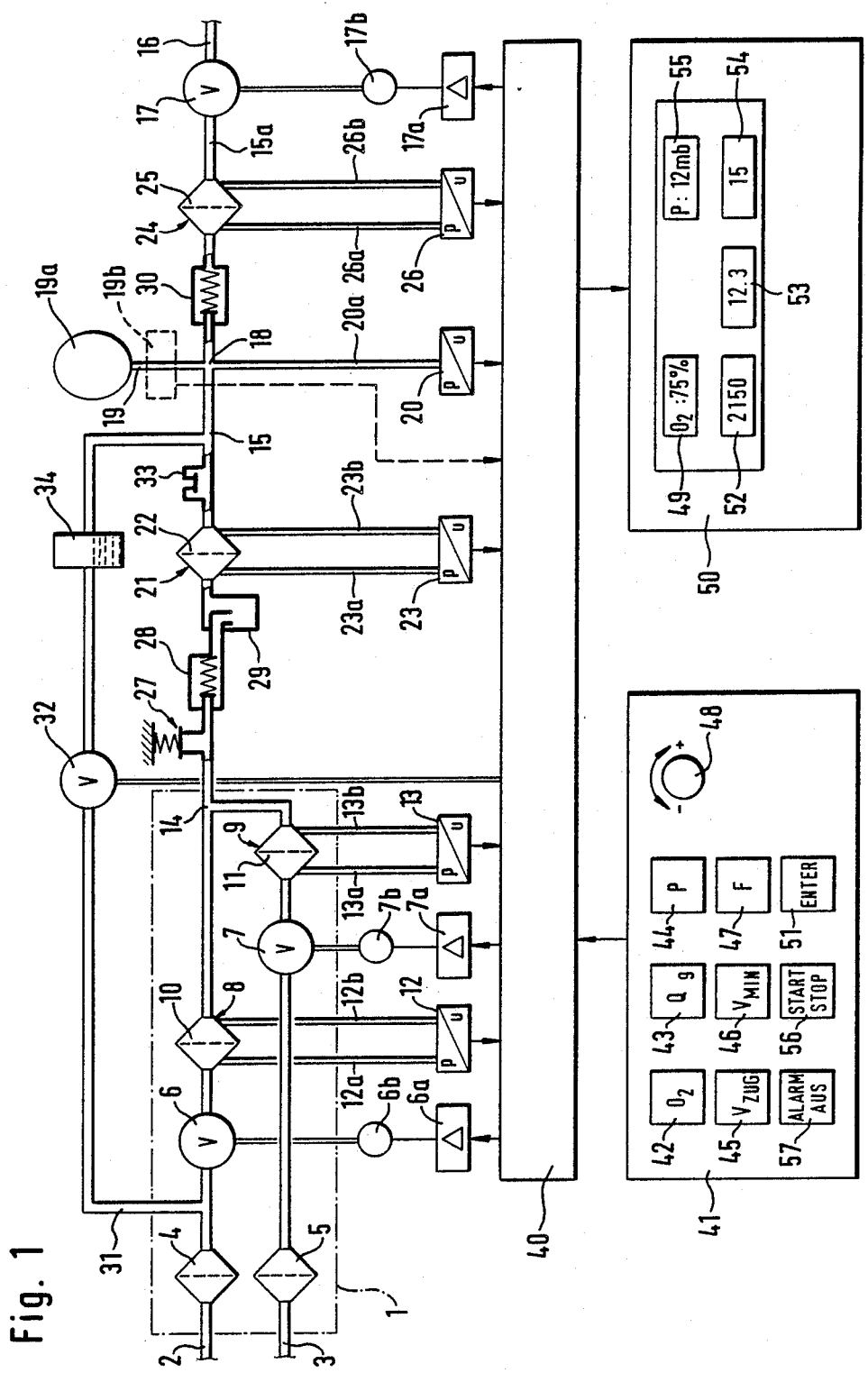
FIG. 1 is a block diagram of an apparatus according to the invention.

The gas-conveying system is illustrated in the upper part of the machine. A respiratory-gas mixing unit 1 contains an air-supply line 2 and an oxygen-supply line 3, on which there are disposed in the flow direction, respectively, a prefilter 4, 5, an air valve 6 or oxygen valve 7 and an air-flow sensor 8 or oxygen-flow sensor 9. The air-flow sensor 8 and the oxygen-flow sensor 9 consist of a flow resistance 10 or 11 and the differential pressure transducer 12 or 13, which are connected together by connecting lines 12a, 12b, 13a, 13b. The design of such gas-flow-measuring devices operating on the differential-pressure principle is known and does not need to be explained further herein.

The air conduit 2 and oxygen conduit 3 are brought together in a mixing area 14. Through a gas duct 15, the mixing area 14 is in communication with an outlet 16 which is open to the atmosphere. An outlet valve 17 is fitted upstream of the outlet 16.

On a junction 18, a patient line 19 branches off to the patient whose lungs are symbolized by the oval 19a. A line 20a to a respiratory-gas pressure sensor 20 also branches off from the junction 18. The respiratory-gas pressure sensor may also be disposed in another location which is in communication with the patient through low-flow resistance lines, so that practically the same pressure prevails at the measuring point as in the patient line, so that the measured pressure coincides with the respiratory-gas pressure of the patient.

A total-fresh-gas-flow sensor 21 consisting of a flow resistance 22, a differential-pressure transducer 23 and connecting lines 23a, 23b, is disposed in the section of the gas duct 15 between the mixing area 14 and the branch pipe 18.

An outlet-flow sensor 24 consisting of a flow resistance 25, a differential-pressure transducer 26 and connecting lines 26a, 26b, is fitted in the section of the gas duct 15 lying between the branch pipe 18 and the outlet 16.

If direct measurement of the patient flow is necessary, the patient-flow sensor 19b, indicated by broken lines in the figure, can be provided in the patient line 19.

A safety valve 27, a first non-return valve 28, a humidifier 29, and a second non-return valve 30 are also located on the gas duct. The non-return valves function in a manner known in itself to prevent reinspiration of spent respiratory air (rebreathing).

The valves 6, 7 are actuated respectively by final control element 6a, 7a and 17a which control an electromagnetic operating mechanism 6b, 7b and 17b, which actuates the actual valve.

In the air conduit 2 an additional line 31 discharges upstream to the air valve 6, and through which air can be taken under the control of a valve 32. The air functions as propellant gas, for example, to produce an aerosol of a drug needed by the patient. An atomizer provided for this purpose is designated 34.

The gas-conveying system in the machine is controlled by means of a central electronic control unit 40. The air-flow sensor 8, the oxygen-flow sensor 9, the total-fresh-gas-flow sensor 22, the outlet-flow sensor 24, the respiratory-gas pressure sensor 20 and, optionally, the patient flow-sensor 19b are connected as input variables to said control unit 40.

The central unit 40 receives further input variables from an input unit 41, delivers the set-point values for the parameters and alarm limits to be set. In the case shown, a button is provided for each such value, and specifically:

button 42 for the set-point value of the oxygen concentration, button 43 for the set-point value of the minimum fresh-gas flow (basic flow), button 44 for the set-point value of the respiratory-gas pressure, button 45 for the alarm limits of the inspiration volume, button 46 for the alarm limits of the respiratory minute volume, and button 47 for the alarm limits of the respiratory rate per minute.

In each case, these values are set by first pressing the button and then adjusting by means of an adjusting knob 48 the value indicated on a corresponding display 49, 52, 53, 54, 55 of an output unit 50. After the desired value has been set, an enter button 51 is pushed in order to transmit the value to the control unit 40.

Further buttons of the input unit 41 are used to turn the machine on and off (start-stop button 56) and to cancel an alarm signal (alarm-off button 57).

The final control elements 6a, 7a and 17a of the valves 6, 7, 17 are also connected to the control unit, whereby the control unit delivers control signals as output signals to the final control elements.

The output variables of the control unit 40 are applied to the output unit 50, where they are displayed by means of appropriate digital displays; display sections are illustrated for the oxygen concentration 49, for the inspiration volume 52, for the respiratory minute volume 53, for the respiratory rate 54 and for the respiratory-gas pressure 55.

In practical operation, the appropriate set-point values are first set by means of the buttons 42, 43 and 44 and the adjusting knob 48 and, if desired, the appropriate alarm limits are set by means of the buttons 45, 46 and 47. Before the machine is turned on, the air conduit 2 and the oxygen conduit 3 must be connected to the corresponding central supply system of the clinic. The patient is connected to the patient line 19 in the normal manner, using a suitable adapter.

After turning on the machine by means of the button 56, the valves 6 and 7 are opened and the two gases are fed through the prefilters 4, 5 and the flow resistances 8, 9 to the mixing area 14. The upstream and downstream pressures prevailing at the flow resistances are supplied, respectively, through the lines 12a, 12b and 13a, 13b to the differential-pressure transducers 12, 13 which produce the actual value of the electrical signal corresponding to the gas flow concerned and transmit it to the control unit 40. In the control unit 40, these actual flow values are compared with the set-point flow values, which were calculated beforehand on the basis of the values for the total flow and the oxygen concentration input into the input unit 41. If deviations between set-point and actual values are observed, the air valve 6 and the oxygen valve 7 are triggered such that the actual values become matched to the set-point values.

As explained hereinabove, the air-control loop (air valve 6, air-flow sensor 8) and the oxygen-control loop (oxygen valve 7, oxygen-flow sensor 9) perform a double function. On the one hand, the respiratory-gas composition is determined by the ratio of the oxygen flow to the air flow and is controlled to correspond to the set-point value that has been set. On the other hand, both control loops are also used for adjustment of the constant respiratory-gas pressure, as will be explained in greater detail hereinbelow.

After preparation of the respiratory-gas mixture in the respiratory-gas mixer 1, the respiratory gas passes to the junction 18 from which the patient line 19 branches off and the which the respiratory-gas pressure transducer 20 is connected. The gas continues to flow to the outlet 16 through the non-return valve 30, the flow resistance 25 of the outlet-flow sensor 24 and the outlet valve 17.

There is added to the flow of the respiratory gas flowing in the gas duct 15 the respiratory flow of the patient (patient line 19), so that a flow which fluctuates with the respiratory rhythm but which is always directed toward the outlet is formed in the expiration branch 15a of the gas duct 15 located downstream of the branch pipe 18 in the direction of flow. Depending on its position, the outlet valve 17 forms a variable flow resistance and thus it influences the pressure at the junction 18 and consequently the respiratory pressure. This actual pressure value is measured by the respiratory-gas pressure sensor 20 and is sent as an electrical voltage to the control unit 40. In the control unit, the actual pressure value is compared with the set-point pressure value (input unit 41, button 44). By means of the final control element 17a, the outlet valve 17 is so controlled on the basis of the corresponding output variable of the control unit 40 that the actual pressure value is restored to the set-point pressure valve.

In the preferred mode of operation described here, the outlet valve 17 is used for brief control of the respiratory-gas pressure. Therefore, it is preferably a valve which is electrically actuated both in the direction of opening and in the direction of closing and which has a short time constant preferably shorter than 0.1 sec., preferably shorter than 0.02 sec., both with respect to the closing behavior and to the opening behavior. Here, as usual, the time constant is defined as the time needed to move the valve 63% of its total travel.

To maintain the CPAP pressure, it is necessary that a flow directed toward outlet 16 always prevail in the expiration branch 15a. During the expiration phase, this flow is ensured by the gas stream from the patient line 19. The total fresh-gas flow passing in the line 15 upstream from the junction 18 can be reduced almost to 0 by means of the respiratory-gas mixing unit 1 during this phase.

For safety reasons, valves that are opened electromagnetically and closed by spring force are preferably used as the air valve 6 and as the gas valve 7. As is true for the outlet valve 17, the time constant of their opening behavior and of their closing behavior ought to be shorter than the cycling period of human respiration. Preferably, it is shorter than 0.1 sec., and especially preferably it is shorter than 0.02 sec. These short time constants permit the possibility of continuously matching the total fresh-gas flow exiting the respiratory-gas mixing unit 1 to the instantaneous demand of the spontaneous respiration of the patient.

The control unit 40 preferably operates by means of a microprocessor on the basis of an appropriate program. Using the information supplied here one skilled in the art can without difficulty devise a control unit that performs the above-described functions. If desired, this can also be accomplished by means of an appropriate special electronic circuit without the use of a microprocessor, but the microprocessor control system is preferred.

Although a specific form of embodiment of the instant invention has been described above and illustrated in the accompanying drawing in order to be more clearly understood, the above description is made by way of example and not as a limitation to the scope of the instant invention. It is contemplated that various modifications apparent to one of ordinary skill in the art could be made without departing from the scope of the invention which is to be determined by the following claims.

We claim:

1. An apparatus for assisting the spontaneous breathing of a patient, comprising:
   a respiratory-gas mixing unit (1) for mixing air and oxygen in a desired ratio in order to supply the patient with a respiratory gas of an adjustable oxygen concentration, said mixing unit including,
   (a) an air conduit (2) having an air flow sensor for generating an electrical air flow signal corresponding to the air flow, and an electrically controlled air valve (6) for adjusting the air flow,
   (b) an oxygen conduit (3) having an oxygen sensor (9) for generating an electrical oxygen flow signal corresponding to the oxygen flow, and an oxygen valve (7) for adjusting the oxygen flow, and
   (c) a mixing area (14) combining said air and oxygen conduits;
   an outlet (16) having
   an electrically controlled outlet valve (17) for adjusting the gas flow through said outlet (16)
   a gas duct (15) connected to said respiratory-gas mixing unit (1) and extending to said outlet (16);
   a patient line (19) branching off from said gas duct (15) for providing an air/oxygen mixture to the patient;
   a respiratory-gas pressure sensor (20) in connection with said patient line for generating an electrical signal corresponding to the pressure of the respiratory-gas in the patient line; and
   an electronic control unit operatively connected to said air flow sensor (8), said oxygen flow sensor (9), said respiratory-gas pressure sensor (20), said air valve (6), said oxygen valve (7), and said outlet valve (17), such that signals from said sensor are input to said control unit as variables, and said control unit outputs control signals to said valves in response thereto.

2. The apparatus of claim 1, further comprising an outlet flow sensor (24), disposed on said gas duct downstream from the junction (18) of said patient line (19) and said gas duct (15), for generating an electrical outlet flow signal corresponding to an output side gas flow, said outlet flow sensor being connected to said control unit.

3. The apparatus of claim 1, further comprising a patient flow sensor (19b) connected to said patient line for generating an electrical patient flow signal corresponding to the actual patient flow of gas, said patient flow sensor being connected to said control unit.

4. The apparatus of claim 1, further comprising an additional total-fresh-gas-flow sensor, disposed between said mixing area (14) and said junction of said patient line (19) and said gas duct (15), for generating an electrical total-fresh-gas-flow signal corresponding to the total-fresh-gas-flow, said total-fresh-gas-flow sensor being connected to said control unit.

5. The apparatus of claim 1, wherein the air valve (6) and the oxygen valve (7) are valves that are opened electromagnetically and are closed by spring force.

6. The apparatus of claim 1, wherein the air valve (6) and the oxygen valve (7) have a time constant which is shorter than 0.1 seconds, both with respect to the closing behavior and to the opening behavior.

7. The apparatus of claim 6, wherein said time constant is shorter than 0.02 seconds.

8. The apparatus of claim 1, wherein the outlet valve (17) is a valve which is electrically actuated both in the direction of opening and in the direction of closing.

9. The apparatus of claim 1, wherein the outlet valve (17) has a time constant which is shorter than 0.1 seconds, both with respect to the closing behavior and to the opening behavior.

10. The apparatus of claim 9, wherein said time constant is shorter than 0.02 seconds.

* * * * *